(12) United States Patent
Pearlstein et al.

(10) Patent No.: US 6,380,254 B2
(45) Date of Patent: Apr. 30, 2002

(54) METHOD AND COMPOSITION FOR TREATING AND PREVENTING PATHOGENIC EFFECTS CAUSED BY INTRACELLULAR CALCIUM OVERLOAD

(75) Inventors: Robert D. Pearlstein, Durham, NC (US); Richard S. Kramer, Millbrae, CA (US)

(73) Assignee: Leigh Biotechnology, Inc., Ponte Vedra Beach, FL (US)

( * ) Notice: Subject to any disclaimer, the term of this patent is extended or adjusted under 35 U.S.C. 154(b) by 0 days.

(21) Appl. No.: 09/804,640

(22) Filed: Mar. 12, 2001

Related U.S. Application Data

(63) Continuation of application No. 09/410,062, filed on Oct. 1, 1999, now abandoned, which is a continuation of application No. 08/939,906, filed on Sep. 29, 1997, now abandoned, which is a continuation of application No. 08/516,181, filed on Aug. 17, 1995, now abandoned, which is a continuation-in-part of application No. 08/188,411, filed on Jan. 24, 1994, now abandoned.

(51) Int. Cl.$^7$ .............................................. A61K 31/195
(52) U.S. Cl. ........................ 514/561; 514/396; 514/399; 514/400; 514/378; 514/538; 514/561; 514/554; 514/557; 514/563; 548/540; 548/335.5; 562/443; 562/553; 562/563; 562/575
(58) Field of Search ................................. 514/532, 538, 514/561, 396, 399, 400, 378, 554, 557, 563, 562; 562/443, 553, 563, 575; 548/540, 335.5

(56) References Cited

U.S. PATENT DOCUMENTS

| | | |
|---|---|---|
| 4,939,146 A | 7/1990 | Kramer et al. |
| 5,028,610 A | 7/1991 | Hirai et al. |
| 5,075,210 A | 12/1991 | Wikman-Coffelt |
| 5,280,038 A | 1/1994 | Kukreja et al. |

OTHER PUBLICATIONS

Dickson et al., "Glycine Cytoprotection During Lethal Hepatocellular Injury From Adenosine Triphosphate Depletion," Gastroenterology 1992; 102:2098–2107.
Paller et al., "Protective Effects of Glutathione, Glycine, or Alanine in An In Vitro Model of Renal Anoxia," J. Am. Soc. Nephrol. 1992; 2:1338–1344.
Butter et al., "Effect of Glycine in Dog and Rat Liver Transplantation," Transplantation, vol. 56; No. 4, pp. 817–822, Oct. 1993.
Nichols et al., "Inhibition of Nonlysosomal Calcium–Dependent Proteolysis by Glycine During Anoxic Injury of Rat Hepatocytes," Gastroenterology 1994; 106:168–176.
Marsh et al., "Glycine Protects Hepatocytes from Injury Caused By Anoxia, Cold Ischemia and Mitochondrial Inhibitors, But Not Injury Caused by Ionophores or Oxidative Stress," Hepatology, vol. 17(1) (1993); pp. 91–98.

Brecht et al., "Protection from hypoxic injury in cultured hepatocytes by glycine, alanine, and serine," Amino Acids, vol. 6, pp. 25–35 (1994).
Engelman et al., "Reduction of infarct size by systemic amino acid supplementation during reperfusion," J. Thorac Cardiovasc Surg 1991; 101:855–59.
Heyman et al., "Mechanism of Glycine Protection in Hypoxic Injury: Analogies with Glycine Receptor," Kidney Int'l., vol. 42 (1992), pp. 41–45.
Almeida et al., "Acute Phosphate Depletion and In Vitro Rat Proximal Tubule Injury: Protection by Glycine and Acidosis," Kidney Int'l., vol. 41 (1992), pp. 1494–1500.
Matheis et al., "Cardiopulmonary Dysfunction Production by Reoxygenation of Immature Hypoxemic Animals Supported by Cardiopulmonary Bypass," J. Thorac Cardiovasc Surg, 105(3): pp. 513–519 (1993).
Julia et al., "Studies of Myocardial Protection in the Immature Heart," J. Thorac Cardiovasc Surg 1991; 101:23–32.
Lazar et al., "Superiority of Substrate Enhancement Over Oxygen Free–Radical Scavengers During Extended Periods of Old Storage for Cardiac Transplantation," Surgery 108(2), pp. 423–430 (1990).
Weinberg et al., "Relationships Between Intracellular Amino Acid Levels and Protection Against Injury to Isolated Proximal Tubules," Am. J. Physiology, 260 (3 Pt 2), pp. F410–19 (1991).
Weinberg et al., "Structural Requirements for Protection by Small Amino Acids Against Hypoxic Injury in Kidney Proximal Tubules," FASEB Journal 4, pp. 3347–3354 (1990).
Rosenkranz et al., Safety of Prolonged Aortic Clamping With Blood Cardioplegia, J. Thorac Cardiovasc Surg 88; pp. 402–410 (1984).
Silva et al., "Effect of Glycine on Medullary Thick Ascending Limb Injury in Perfused Kidneys," Kidney International, vol. 39, pp. 653–568 (1991).

(List continued on next page.)

Primary Examiner—Shailendra Kumar
(74) Attorney, Agent, or Firm—Finnegan, Henderson, Farabow, Garrett & Dunner, L.L.P.

(57) ABSTRACT

The present invention provides a method and composition for treating or preventing pathogenic effects in a mammal caused by intracellular calcium overload, comprising administering to a mammal a mixture of sodium co-transport dependent amino carboxylic acids or their physiologically acceptable salts in an amount sufficient to substantially saturate sodium-dependent amino carboxylic acid transport mechanisms of a cell's plasma membranes. Administration of these amino carboxylic acids can advantageously treat or prevent cell lysis and irreversible cell damage caused by intracellular calcium overload, especially in mammals suffering from a disease condition associated with or resulting from insufficient tissue oxygenation.

15 Claims, No Drawings

OTHER PUBLICATIONS

Singh J. et al., "Effect of Asparate and Glutamate on Experimental Myocardial Infarction in Rats," Indian J. Exp. Biol., vol. 27:621–624 (1989).

Weinberg et al., "Amino Acid Protection of Cultured Kidney Tubule Cells Against Calcium Ionophore–Induced Lethal Cell Injury," vol. 65, No. 6, pp. 671–678 (1991).

Abe et al., "Recovery from Calcium–Induced Damage in a Neuroblastoma Cell Line," Brain Research, 423 (1987), pp. 221–228.

Tymianski et al., "Secondary $Ca^{2+}$ Overload Indicates Early Neuronal Injury Which Precedes Staining With Visibility Indicators," Brain Research, 607 (1993), p. 319–323.

Lehmann et al., "In Vivo Regulation of Extracellular Taurine and Other Neuroactive Amino Acids in the Rabbit Hippocampus," Taurine: Biological Actions and Clinical Perspectives, (1985), pp. 289–311.

Altschuld et al., "Response of Isolated Rat Heart Cells to Hypoxia, Re–Oxygenation, and Acidosis," Circulation Research 49(2):307–16, Aug. 1981.

Anundi et al., "Fructose Prevents Hypoxic Cell Death in Liver," American Journal of Physiology, 253 (3 Pt 1):G390–6, Sep. 1987.

Bonventre et al., "Effects of Metabolic Acidosis on Viability of Cells Exposed to Anoxia," American Journal of Physiology, 249 (1 Pt 1):C149–59, Jul. 1985.

Gores et al., "Extracellular Acidosis Delays Onset of Cell Death in ATP–depleted hepatocytes," American Journal of Physiology, 255 (3 pt 1):C315–22, Sep. 1988.

Penttila et al., "Extracellular Acidosis Protects Ehrlich Ascites Tumor Cells and Rat Renal Cortex Against Anoxic Injury," Science, 185(147):277–8, Jul. 19, 1974.

Kim–Lee et al., Dissertation Abstract Internation. vol. 52, No. 11B, p. 5694. Abstract only, 1991.

Dixon et al., Am. J. Physiology, 253, H1026–34. Abstract only, 1987.

Rote Liste 1992.

ively in the extent of organ damage or hypoxic or post-hypoxic cell lysis in a mammal that has suffered from a disease condition associated with or resulting from insufficient tissue oxygenation.

METHOD AND COMPOSITION FOR TREATING AND PREVENTING PATHOGENIC EFFECTS CAUSED BY INTRACELLULAR CALCIUM OVERLOAD

This is a continuation of application Ser. No. 09/410,062 filed Oct. 1, 1999, now abandoned, which is a continuation of Ser. No. 08/939,906, filed Sep. 29, 1997, now abandoned, which is a continuation of Ser. No. 08/516,181, filed Aug. 17, 1995, now abandoned, which is a continuation-in-part of Ser. No. 08/188,411, filed Jan. 24, 1994, now abandoned, all of which are now abandoned, and incorporated herein by reference.

BACKGROUND OF THE INVENTION

The present invention relates to a method and composition for treating and preventing pathogenic effects in mammals caused by intracellular calcium overload. Calcium overload occurs in the tissue and organs of mammals suffering from a disease condition associated with or resulting from insufficient tissue oxygenation. By treating the pathogenic effects of intracellular calcium overload, the present invention also effectively prevents irreversible cell damage and cell lysis in cells transiently deprived of oxygen.

Healthy cells regulate free cytosolic calcium concentrations by limiting influx of the cation across the cell's plasma membrane, sequestering free calcium, and pumping calcium ions out of the cytosol. When a cell becomes ischemic, insufficient free energy exists to operate the ion pumps. As calcium accumulates in the cytosol, degradative enzymes become activated and begin to further affect the cell's ability to regulate calcium. Calcium activated enzymes, e.g., phospholipases, break down the cell's membranes, making them even "leakier" to calcium. Additional enzymes, e.g., proteases, also attack the molecular pumps. When oxygen is restored to the tissue, free radical oxygen species are produced that can further damage these systems.

If the combined effects of the enzymes and the free radical oxygen species becomes severe enough, the cell will not recover and maintain acceptable levels of calcium, even if it successfully re-energizes when circulation is reestablished. The cell has become irreversibly damaged and will ultimately die from an overload of calcium. This pathogenic sequence might be repeated millions of times in the first several hours following a transient interruption in blood supply to the heart or brain.

Neuron damage, following a stroke or cardiac arrest, and myocyte damage, following coronary artery occlusion, are two examples of such cell damage. When essential cellular constituents leak out of such damaged cells, the cell is referred to as lysed and, of course, is irreparable.

Various treatments have been studied for treating or preventing calcium mediated cellular damage to reduce the likelihood of cell lysis during and following a transient period of oxygen deprivation. The most common treatments involve administering chemical compounds that either limit entry of calcium ions into the cell (i.e., plasma membrane channel blockers) or antagonize the calcium activated enzymes by binding to intracellular proteins like calmodulin. These treatments, however, are not restricted to the damaged cells. They can affect the function of normal, healthy cells and cause a number of adverse side effects. More selective methods are, therefore, needed to treat or prevent calcium mediated damage in cells deprived of oxygen, while avoiding these adverse side effects.

SUMMARY OF THE INVENTION

It is an object of the present invention to treat or prevent the pathogenic effects in a mammal caused by intracellular calcium overload. It is another object to prevent irreversible cell damage or hypoxic or post-hypoxic cell lysis in a mammal that has suffered from a disease condition associated with or resulting from insufficient tissue oxygenation.

It is a more specific object of the present invention to provide methods and compositions for preventing lysis of such cells and reducing the extent of organ damage in a mammal that has suffered from anoxia, hypoxia or ischemia, such as that which occurs in cardiac arrest, pulmonary embolus, renal artery occlusion, coronary artery occlusion, occlusive stroke, hemorrhagic stroke, adult respiratory distress syndrome, neonatal respiratory distress syndrome, suffocation, or profound anemia.

Additional objects and advantages of the invention will be set forth in part in the description which follows, and in part will be apparent from the description, or may be learned by practice of the invention. The objects and advantages of the invention may be realized and obtained by means of instrumentalities and combinations particularly pointed out in the appended claims.

To achieve the objects and in accordance with the purpose of the invention, as embodied and broadly described herein, the invention comprises a method for treating or preventing pathogenic effects in a mammal caused by intracellular calcium overload comprising administering to the mammal a mixture of sodium co-transport dependent amino carboxylic acids or their physiologically acceptable salts in an amount sufficient to substantially saturate the sodium dependent amino carboxylic acid transport mechanisms of a mammalian cell's plasma membrane. The present invention also relates to a pharmaceutical composition for treating or preventing pathogenic effects in a mammal caused by intracellular calcium overload that comprises a mixture of sodium co-transport dependent amino carboxylic acids or their physiologically acceptable salts in an amount sufficient to substantially saturate the sodium dependent transport mechanisms of a mammalian cell's plasma membrane to treat or prevent these pathogenic effects, together with a pharmaceutically acceptable carrier.

As used in the present invention, the terms "saturate" and "saturating concentrations" denote the accepted biochemical kinetic definition, i.e., those concentrations of substrate or ligand that maximally activate ($V_{max}$) their respective enzyme(s), transport mechanism(s), or receptor(s).

Reference will now be made in detail to preferred embodiments of the invention.

DETAILED DESCRIPTION OF THE INVENTION

An aspect of the present invention contemplates treating a mammal suffering with a disease condition resulting from insufficient tissue oxygenation by administrating a mixture of therapeutic amino carboxylic acid agents to alleviate the toxic effects of calcium overload on hypoxic and/or post hypoxic cells, anoxic and/or postanoxic cells, and ischemic and/or postischemic cells. The therapeutic amino carboxylic acids of the present invention can treat such cells by entering the cell's interiors. They are referred to as sodium co-transport dependent amino carboxylic acids. To be sodium co-transport dependent means that these amino carboxylic acids are obligatorily transported into the cell in association with sodium through sodium dependent, plasma membrane transport systems.

Without being bound to any particular theory, it is believed that when the amino carboxylic acids of the present invention enter the cell with the sodium ions they cause a partial discharge of the cell membrane's sodium electrochemical gradient. This disturbance in the gradient prevents rapid re-alkalinization of the cell, thereby inactivating pH-sensitive calcium dependent cytolytic enzymes and minimizing or eliminating the cytotoxic effects of calcium overload. All of the therapeutic amino carboxylic acid agents of the present invention are selective for identified sodium-dependent transport ("symport") proteins. The sodium dependent transport systems are known to those skilled in the art to include the GLY, A, ASC, and N transporters.

In a primary embodiment of the present invention, a pharmaceutical composition is provided containing saturating concentrations of:

(a) one or more substrates for the GLY transport system;

(b) one or more substrates for the A transport system;

(c) one or more substrates for the ASC transport system;

(d) one or more substrates for the N transport system; and (e) at least one stimulator or activator of the hepatic urea cycle.

A preferred composition of these substrates comprises a mixture of glycine, proline, histidine, serine, alanine, glutamic acid, glutamine, and arginine.

As indicated, in this embodiment, one or more administered therapeutic agents are substrates for the "GLY" transport system. The GLY transport system is a sodium-dependent amino carboxylic acid transport protein widely expressed in terminally differentiated mammalian cells. See H. N. Christensen, Physiological Reviews, Volume 70, p. 43–77, 1990, hereby incorporated by reference. The preferred substrate for the GLY symport is glycine.

The amino carboxylic acid substrates for the sodium dependent "A" transport system include metabolizable model substrates, alanine or proline, or non-metabolizable substrates, 2-aminoisobutyric acid or N-methyl-alpha-aminoisobutyric acid. The preferred substrate for the A symport is -alanine. An amino carboxylic acid substrate for the sodium dependent "ASC" transport system is serine. Both the A and ASC transport systems are expressed in terminally differentiated mammalian cells. See, H. N. Christensen, supra.

A substrate for another sodium-dependent amino carboxylic acid transport protein, the "N" transport system, which expresses specific terminally differentiated mammalian cells like hepato-cytes, H. N. Christensen supra. includes amino carboxylic acids selected from histidine, asparagine, glutamic acid, or glutamine. The preferred substrate for the N symport is histidine.

Some of the amino carboxylic acids of the present invention can also stimulate the hepatic urea cycle in a mammal. This is important in situations where administration of a particular acid exceeds hyper-physiological amounts, creating potential toxicity concerns. With the hepatic urea cycle stimulating amino carboxylic acids of the invention, however, one can advantageously increase dosage amounts of the other amino carboxylic acids, in some cases above the hyper-physiological amounts. The preferred hepatic urea cycle stimulating amino carboxylic acid is arginine.

Additional therapeutically active agents can be co-administered with these sodium co-transport dependent amino carboxylic acids of the present invention. Examples of classes of agents that may complement the action of the therapeutic amino carboxylic acids of the present invention include:

(1) a plasma volume expander, such as dextran;

(2) a water soluble magnesium salt, such as magnesium chloride;

(3) a thrombolytic enzyme, such as streptokinase;

(4) scavengers of toxic oxygen metabolites, such as superoxide dismutase and/or catalase;

(5) a xanthine oxidase inhibitor, such as allopurinol; and (6) a substance which binds free iron, such as desferrioxamine.

The amino carboxylic acids contemplated for use in the present invention can be obtained in various ways, including hydrolysis of a protein or fermentation of glucose, for example. Amino acids have also been created in the laboratory by passing an electric discharge through a mixture of ammonia, methane, and water vapor. Hawley, "The Condensed Chemical Dictionary," 10th Ed., 1981, pp. 48–49.

The amino carboxylic acids of the present invention can be administered in intravenous infusions after a hypoxic, anoxic, or ischemic condition occurs to treat or prevent irreversible cell injury and cell lysis caused by intracellular calcium overload. For example, the amino carboxylic acids of the present invention can be administered by intravenous infusion immediately after a cerebral infarction, a myocardial infarction, asphyxia, or cardiopulmonary arrest. Alternatively, the amino carboxylic acids can be administered by intravenous or intra-arterial infusion concurrently and in association with thrombolytic therapy.

The therapeutic agents of the present invention can be used prophylactically in surgical settings where circulation to an organ or organ system is deliberately interrupted, e.g. coronary artery bypass surgery, tissue grafting, endarterectomy, angioplasty, etc. The present invention also contemplates adding the amino carboxylic acids to a cardioplegia solution for organ perfusion, and to perfusion and preservative solutions for organ transplantation.

The amino carboxylic acids of the present invention can be administered in mixtures with one another, or together with a physiologically suitable carrier or vehicle. If appropriate, the aramino carboxylic acids may be administered in the form of a physiologically acceptable salt, for example, an acid addition salt. A preferred carrier is 5% dextrose in water or half-strength normal saline, buffered to pH 7.4 with a physiologically acceptable buffer substance.

In administering the amino carboxylic acids of the present invention, a loading dose is given at the start of treatment. Thereafter, a maintenance dose is to be administered either continuously or intermittently in order to maintain optimal levels of the amino carboxylic acids in the blood. The timing and amount of the maintenance dose can be determined by intermittently monitoring the levels of the amino carboxylic acids in the blood.

The amount of amino carboxylic acids administered as a loading or maintenance dose will depend upon the particular acids employed, the number of acids administered, and the method of application. Due to the potentially toxic effects of hyper-physiological concentrations of amino carboxylic acids in the blood, they are typically administered so as to attain a blood plasma concentration of no greater than 200 to 300 milligrams total free amino carboxylic acid per deciliter (100 ml) of blood. As mentioned above, however, if an hepatic cycle stimulating amino carboxylic acid of the present invention is co-administered, it is possible to increase the dosage amount.

In accordance with a preferred embodiment of the present invention, there is provided a mixture of glycine, proline, histidine, serine, alanine, glutamic acid, glutamine, and arginine administered by intravenous infusion into a 70 kg mammal. In this embodiment, the acids can be dissolved in one liter of a suitable water based carrier to a concentration of between 0.5–0.7% glycine (0.6% being preferred), between 0.6–0.9% proline (0.8% being preferred), between 0.8–1.2% histidine (1.0% being preferred), between 0.5–0.8% serine (0.7% being preferred), between 0.5–0.7% alanine (0.6% being preferred), between 0.3–0.5% glutamic acid (0.4% being preferred), between 0.3–0.5% glutamine (0.4% being preferred), and between 0.4–0.6% arginine (0.5% being preferred). A large volume loading dose of from about 2 to 3 ml per kg of body weight is first administered over a period of 30 minutes. Thereafter, a maintenance dose of about 1 to 2 ml per kg of body weight per hour is administered for 4 to 6 hours. Further administration of the therapeutic solution is determined by monitoring the blood amino carboxylic acid levels in order to maintain a total blood concentration of total amino carboxylic acids of between 200 to 300 mg per deciliter (100 ml) of blood. Treatment can continue for at least 12 hours after tissue oxygenation is normalized.

The above embodiment (corrected for the effect of dilution in total body water) has been demonstrated to achieve near or substantial saturation of the sodium-dependent amino carboxylic acid transporters of the hepatocyte plasma membrane. Analogous concentrations of these eight constituent amino carboxylic acids were employed in the "Mixture" described in Examples 2–7 below.

A particularly preferred embodiment, described in Example 8, comprises a mixture of 8 amino carboxylic acids formulated as a dry powder that is to be reconstituted as a buffered intravenous solution with 5% dextrose (or half strength normal saline). The amino acids comprising this mixture are those whose entry into mammalian cells is mediated by one or more of the sodium-dependent plasma membrane transport systems: alanine, proline, histidine, serine, glycine, glutamine, glutamic acid, and arginine. In this embodiment, the following amino carboxylic acids can be dissolved by gram amounts in one liter of a suitable water-based carrier: between 7 g to 34 g alanine (between 20 g to 30 g being preferred, and 30 g particularly preferred); between 9 g to 42 g proline (between 28 g to 40 g being preferred, and 35 g particularly preferred); between 8 g to 28 g histidine (between 10 g to 24 g being preferred, and 15 g particularly preferred); between 8 g to 34 g serine (between 14 g to 30 g being preferred and 20 g particularly preferred); between 7 g to 38 g glycine (between 15 g to 35 g being preferred, and 32 g particularly preferred); between 5 g to 34 g glutamine (between 14 g to 30 g being preferred, and 21 g particularly preferred); between 1 g to 9 g glutamic acid (between 2 g to 6 g being preferred, and 4 g particularly preferred); and between 6 g to 58 g arginine (between 30 g to 52 g being preferred, and 43 g particular preferred).

The relatively high concentrations of the eight amino carboxylic acids of the particularly preferred embodiment (described above) are designed to fully saturate the sodium-dependent transport mechanisms not only of hepatocytes, but also of essentially all other mammalian cells considered to be susceptible to calcium overload. An initial dosing of the particular preferred embodiment is about 1.0 gm/Kg of body weight given over 60 minutes, and the maintenance dose is about 0.2 gm/Kg/hour for a period of 6 to 12 hours or longer as clinical implications warrant.

The suitability of the therapeutic acids of the present invention for treating or preventing irreversible cell damage and cell lysis caused by intracellular calcium overload can be predicted from the following examples.

EXAMPLE 1

Hepatic cells were isolated from rat livers by the method described in P.O. Seglen, "Preparation of Rat Liver Cells", Experimental Cell Research Vol. 82, pp. 391–398, 1973, with several modifications. The liver was initially perfused through the v. porta with 250 ml of a 37° C., oxygen saturated buffered salt solution (BSS: 144 mM NaCl, 5 mM KCl, 5 mM NaHCO$_3$, 1 mM NaH$_3$PO$_4$ and 10 mM HEPES, pH 7.4) containing 10 mM a EGTA, followed by 300 ml of warm, oxygenated BSS containing 50 mg collagenase (Worthington Type II, 175 units/mg) and 1.3 mM CaCl$_2$. Both perfusates were introduced in situ at a rate of 20 ml/minute. The liver was dispersed by several passages through a glass pipette tip (4 mm aperture), subsequently filtered through two layers of a 250 micron Nylon mesh, and diluted in 50 ml of a chilled suspension medium of the BSS containing 1.3 mM CaCl$_2$, 1.3 mM MgCl$_2$, 20 mM glucose, and 5 mM pyruvate. The crude suspension was purified by differential centrifugation (100 g per 2 minutes).

The purified cell suspension, consisting primarily of liver parenchymal cells, was washed three times with the cold suspension medium. The final pellet was resuspended at a concentration of 20 mg cell protein (Biuret assay) per milliliter of suspension medium and incubated aerobically for one hour at 24° C. in a 50 ml polypropylene centrifuge tube mounted horizontally on the rocker tray of a shaking water bath (30 strokes per minute). At the end of this incubation period, hepatocyte viability was assessed by trypan blue exclusion. Suspensions exhibiting less than 80% viability were discarded.

Samples of the purified cell suspension were then transferred to two 50 ml polypropylene test tubes. One of these tubes was purged of oxygen by flushing the gas phase with argon and then permitting the cells to consume the residual oxygen in the medium. Anaerobiosis was attained within 3 minutes as determined polarographically. This anaerobic suspension was maintained in a 37° C.. water bath without agitation.

The other test tube was supplemented with oxygen by flushing the gas phase with pure oxygen. Diffusion of oxygen from the gas phase to this aerobic reference cell suspension was encouraged by orienting the tube in such a fashion as to maximize surface area and by gently agitating the suspension in the 37° C.. water bath. After 90 minutes, both suspension were removed from the water bath and the cells were washed two times with an ice cold suspension buffer and then resuspended in a warm, aerated suspension medium to a concentration of 10 mg cell protein.

A one milliliter sample of the anaerobic suspension was added to 4 ml of warm, aerated suspension medium containing either no additives (for the untreated cells), or a single amino carboxylic acid at a concentration of 5 mM. Cell viability was assessed in each test population at the end of a subsequent 90 minute aerobic incubation at 37° C. by measuring the fraction of cytosolic lactate dehydrogenase activity retained intracellularly. The results of these viability assessments are reported in Table 1 as follows:

TABLE 1

| TREATMENT | SURVIVING FRACTION |
| --- | --- |
| Untreated | 0.25 |
| Glycine | 0.53 |
| Histidine | 0.50 |
| Asparagine | 0.54 |
| Glutamine | 0.52 |
| Glutamic acid | 0.52 |
| Alanine | 0.51 |
| Arginine | 0.51 |

TABLE 1-continued

| TREATMENT | SURVIVING FRACTION |
|---|---|
| Cysteine | 0.49 |
| Proline | 0.49 |
| Serine | 0.40 |
| Valine | 0.28 |
| Leucine | 0.32 |
| Tyrosine | 0.31 |
| Isoleucine | 0.29 |

The data in Table 1 demonstrates the effectiveness of sodium co-transport dependent amino carboxylic acids (e.g., glycine, histidine, asparagine, glutamine, glutamate, alanine, arginine, glycine, proline, and serine) in preventing loss of cell viability normally associated with a transient period of oxygen deprivation. This data also demonstrates the effectiveness of the sodium co-transport dependent amino carboxylic acids (transported into the cell in association with sodium by the activity of sodium dependent, plasma membrane transport systems, as described above) to preserve cell viability as compared with other amino carboxylic acids such as valine, leucine tyrosine, and isoleucine, which are not substrates for the sodium dependent, plasma membrane transport systems.

EXAMPLE 2

Using the procedure set forth in Example 1, the effectiveness of chlorpromazine, a calcium antagonist and widely recognized cytoprotectant, in preserving cell viability following a 90 minute period of oxygen deprivation was compared to a specific sodium co-transport dependent amino carboxylic acid and a mixture of these acids, i.e., glycine and a mixture of glycine, proline, histidine, serine, alanine, glutamic acid, glutarnine, and arginine.

Hepatocytes were incubated anaerobically for 90 minutes, then washed and resuspended in fresh medium containing either no additives (for the untreated cells), chlorpromazine (25 $\mu$M), glycine (20 mM or 150 mg per 100 ml, a saturating concentration), or the aforementioned (near or substantially saturating) mixture of amino carboxylic acids (total amino carboxylic acid concentration was less than 5 mM or 65 mg per 100 ml). Cell viability was assessed as the fraction of the cytosolic enzyme, lactate dehydrogenase, retained intracellularly following a 90 minute aerobic incubation. A minimum of four observations were made and recorded. The results are reported in Table 2 as the mean surviving fraction with standard deviation as follows:

TABLE 2

| TREATMENT | MEAN SURVIVING FRACTION |
|---|---|
| Untreated | .342 ± .067 |
| Chlorpromazine | .567 ± .055 |
| Glycine | .698 ± .065 |
| Mixture | .578 ± .092 |

The data from Table 2 demonstrates the effectiveness of the mixture of amino carboxylic acids in preserving cell viability following a period of oxygen deprivation. It also demonstrates that the amino carboxylic acid mixture of the present invention provides comparable protection against cell lysis compared with the well known calcium antagonist, chlorpromazine.

EXAMPLE 3

Using the procedure set forth in Example 1, the effectiveness of trifluoperazine, another widely recognized cytoprotectant and calcium antagonist, in preserving cell viability following a 90 minute period of oxygen deprivation was compared to glycine and the mixture of amino carboxylic acids containing the same acids as in Example 2.

Hepatocytes were incubated anaerobically for 90 minutes, then washed and resuspended in fresh medium containing either no additives (untreated cells), trifluoperazine (25 $\mu$M), glycine (20 mM or 150 mg per 100 ml), or a mixture of amino carboxylic acids (total amino carboxylic acid concentration was less than 5 mM or 65 mg per 100 ml). Cell viability was assessed as the fraction of lactate dehydrogenase retained intracellularly following a 90 minute aerobic incubation. A minimum of four observations were made and recorded. The results are reported in Table 3 as mean surviving fraction as follows:

TABLE 3

| TREATMENT | MEAN SURVIVING FRACTION |
|---|---|
| Untreated | .384 ± .007 |
| Trifluoperazine | .550 ± .061 |
| Glycine | .739 ± .014 |
| Mixture | .626 ± .033 |

As seen from the data of Table 3, the amino carboxylic acid mixture of the present invention demonstrated superior ability in preserving cell viability following a period of oxygen deprivation as compared with the known calcium antagonist, trifluoperazine.

EXAMPLE 4

Using the procedure set forth in Example 1, the effectiveness of neomycin sulfate, a calcium channel blocker, in preserving cell viability following a 90 minute period of oxygen deprivation was compared to glycine and the mixture of amino carboxylic acids mentioned above.

Hepatocytes were incubated anaerobically for 90 minutes, then washed and resuspended in fresh medium containing either no additives (for the untreated cells), neomycin sulfate (10 mM), glycine (20 mM or 150 mg per 100 ml), or the mixture of amino carboxylic acids (total amino carboxylic acid concentration was less than 5 mM or 65 mg per 100 ml). Cell viability was assessed as the fraction of lactate dehydrogenase retained intracellularly following a 90 minute aerobic incubation. A minimum of four observations were made and recorded. The results are reported in Table 4 as the mean surviving fraction as follows:

TABLE 4

| TREATMENT | MEAN SURVIVING FRACTION |
|---|---|
| Untreated | .384 ± .040 |
| Neomycin Sulfate | .566 ± .043 |
| Glycine | .694 ± .033 |
| Mixture | .578 ± .044 |

The data from Table 4 demonstrates the ability of the amino carboxylic acid mixture of the present invention to provide comparable protection against cell lysis as compared with the well known calcium channel blocker, neomycin sulfate.

EXAMPLE 5

Using the procedure set forth in Example 1, the effectiveness of alpha-tocopherol, an antioxidant and free radical scavenging cytoprotectant, in preserving cell viability following a 90 minute period of oxygen deprivation was compared to glycine and the mixture of amino carboxylic acids.

Hepatocytes were incubated anaerobically for 90 minutes, then washed and resuspended in fresh medium containing either no additives (for the untreated cells), alpha tocopherol succinate (100 mg per 100 ml), glycine (20 mM or 150 mg per 100 ml), or the mixture of amino carboxylic acids (total amino carboxylic acid concentration was less than 5 mM or 65 mg per 100 ml). Cell viability was assessed as the fraction of lactate dehydrogenase retained intracellularly following a 90 minute aerobic incubation.

A minimum of 4 observations were made and recorded. The results were reported in Table 5 as the mean surviving fraction as follows:

TABLE 5

| TREATMENT | MEAN SURVIVING FRACTION |
|---|---|
| Untreated | .352 ± .050 |
| alpha-tocopherol | .421 ± .087 |
| Glycine | .749 ± .020 |
| Mixture | .635 ± .029 |

The data from Table 5 demonstrates the superiority of the amino carboxylic acid mixture of the present invention in preserving cell viability as compared with alpha-tocopherol.

EXAMPLE 6

Using the procedure set forth in Example 1, the effectiveness of desferrioxamine, a scavenger of delocalized iron and well known cytoprotectant, in preserving cell viability following a 90 minute period of oxygen deprivation was compared to glycine and the amino carboxylic acid mixture.

Hepatocytes were incubated anaerobically for 90 minutes, then washed and resuspended in a fresh medium containing either no additives (for the untreated cells), desferrioxamine (25 $\mu$M), glycine (20 mM or 150 mg per 100 ml), or the mixture of amino carboxylic acids (total amino carboxylic acid concentration was less than 5 mM or 65 mg per 100 ml).

Cell viability was assessed as the fraction of lactate dehydrogenase retained intracellularly following a 90 minute aerobic incubation. A minimum of 4 observations were made and recorded. The results are reported in Table 6 as the mean surviving fraction as follows:

TABLE 6

| TREATMENT | MEAN SURVIVING FRACTION |
|---|---|
| Untreated | .363 ± .022 |
| Desferrioxamine | .393 ± .029 |
| Glycine | .696 ± .038 |
| Mixture | .582 ± .051 |

The data in Table 6 clearly demonstrates the superiority of the amino carboxylic acid mixture of the present invention in preserving cell viability as compared with desferrioxamine.

EXAMPLE 7

Using a modification of the procedure set forth in Example 1, the effect of the amino carboxylic acid mixture of the present invention on intracellular calcium activity was assessed by monitoring the activity of glycogen phosphorylase "a" in cells retaining intracellular enzymes 90 minutes after oxygen deprivation. Glycogen phosphorylase (E.C.2.4.1.1) is converted from the "b" form to the "a" form by phosphorylase kinase. Kinase is stimulated by increased intracellular calcium concentration via calmodulin. The measured activity of phosphorylase "a" in isolated cells has been shown to be directly related to cytosolic calcium activity by Long and Moore, as published in J. Pharmacal. Expt. Thera., Vol. 238, pp. 186–191, 1986.

Hepatocytes were incubated anaerobically for 90 minutes, then washed and resuspended in fresh medium containing either no additives (for the untreated cells), chlorpromazine (25 $\mu$M), glycine (20 mM or 150 mg per 100 ml), or the mixture of amino carboxylic acids (total amino carboxylic acid concentration was less than 5 mM or 65 mg per 100 ml). Cell viability was assessed as the fraction of lactate dehydrogenase retained intracellularly following a 90 minute aerobic incubation. Intracellular calcium activity was assessed in these post-anaerobic cells by the method described in Long and Moore, supra, and expressed in terms of glycogen phosphorylase a activity. The activity is determined by the number of mmols of $PO^-_3$ liberated from a standard amount of glucose-1-phosphate in the presence of glycogen and caffeine, following the addition of 1 million viable, post-anaerobic cells to a lysing buffer. A minimum of four observations were made and recorded. The results are reported in Table 7 as mean surviving fraction as follows:

TABLE 7

| TREATMENT | GLYCOGEN PHOSPHORYLASE A ACTIVITY |
|---|---|
| Untreated | 165.5 ± 49.2 |
| Chlorpromazine | 129.1 ± 36.5 |
| Glycine | 124.8 ± 22.9 |
| Mixture | 131.8 ± 44.7 |

The data in Table 7 demonstrates the effectiveness of an amino carboxylic acid mixture of the present invention in reducing intracellular calcium activity following a period of oxygen deprivation. The data also demonstrates that the present invention provides comparable inhibition of calmodulin mediated processes in post-anaerobic cells as compared with the calcium antagonist, chlorpromazine.

EXAMPLE 8

A particularly preferred embodiment comprises a mixture of 8 amino carboxylic acids formulated as a dry powder that is to be reconstituted as a buffered intravenous solution with 5% dextrose (or half strength normal saline). The amino carboxylic acids comprising this mixture are those whose entry into mammalian cells is mediated by one or more of the sodium-dependent plasma membrane transport systems: alanine, proline, histidine, serine, glycine, glutamine, glutamic acid, and arginine.

Composition

The composition of the standard mixture to be reconstituted in 1 liter of buffered physiological diluent is as follows:

TABLE 8

| AMINO CARBOXYLIC ACID | GRAMS |
|---|---|
| Alanine | 30 |
| Proline | 35 |
| Histidine | 15 |
| Serine | 20 |
| Glycine | 32 |

TABLE 8-continued

| AMINO CARBOXYLIC ACID | GRAMS |
|---|---|
| Glutamine | 21 |
| Glutamic acid | 4 |
| Arginine | 43 |

Indications

A primary application of this particularly preferred embodiment includes treating myocardial infarction. This embodiment can also treat ischemic and post-ischemic tissue in general, as well as the treatment or prophylaxis of a variety of ischemic conditions, both pathologic (e.g., pulmonary embolus, peripheral arterial thrombosis) and iatrogenic (e.g., coronary bypass surgery, cardioplegia). This particularly preferred embodiment can be further modified to treat primary neural ischemia, e.g., stroke, spinal cord injury, cerebrovascular surgery, etc. In this modification, additional arginine (a urea cycle stimulant) is substituted for glutamic acid, in recognition of the injured brain's heightened sensitivity both to the neuroexcitatory transmitter and to ammonia.

The above-described, particularly preferred embodiment exerts a favorable effect on cell survival if administered as long as 90 minutes or so after the onset of an acute ischemic insult, and continued for at least three hours thereafter. Preferably, treatment should be initiated as soon as the diagnosis of acute myocardial infarction or other ischemic or hypoxic injury is entertained, rather than waiting hours or days for confirmation. Furthermore, treatment should be continued for at least 12 hours thereafter, or as long as additional tissue re-perfusion can reasonably be anticipated.

Administration

The above-described, particularly preferred embodiment is formulated as a dry powder and reconstituted into a sterile, non-pyrogenic solution in a single dose container for intravenous administration. The preferred solvent is 5% dextrose in water, and the final volume is one (1) liter. The pH is adjusted with sodium hydroxide. The mixture is not inherently light or oxygen sensitive; however, a preservative such as sodium hydrosulfite (20 mg %) may be used.

The intravenous solution can be administered peripherally via a relatively large-bore (e.g., 16 gauge) "intra-cath" type of cannula, or centrally following accepted catheter placement technique; the infusing tubing should include an in-line filter. Since the 20% solution is distinctly hypertonic with respect to plasma, the usual precautions against extravasation should be observed.

Therapy preferably should start as soon as the diagnosis of possible myocardial infarction or other ischemic or hypoxic injury is considered. An intravenous loading dose of 1.0 gm/Kg is administered over an interval of 60 minutes (0.083 ml//Kg/min×60 minutes). The initial 25–50% of the loading dose could be infused by "IV push" over the first 10–20 minutes, if hemodynamic parameters and blood volume considerations permit. The loading dose is followed with maintenance doses of 0.2 gm/Kg/hour (0.017 ml/Kg/min) for at least 12 hours, or as indicated. The maintenance dose may be adjusted based on periodic measurements of plasma amino carboxylic acid and electrolyte concentrations; the desired plasma amino car boxylic acid level is 15–25 mM (normal=2.1–3.9 mM).

The above embodiment may be supplemented with potassium (up to 60 mEq/liter KCl). Other drugs as described previously may be co-administered via a separate route, such as thrombolytic agents, anti-arrhythmnics, beta-blockers, etc.

It will be apparent to those skilled in the art that various modifications and variations can be made in the present invention without departing from the scope or spirit of the invention. Thus it is intended that the present invention cover the modifications and variations of this invention provided that they come within the scope of the appended claims or their equivalents.

What is claimed is:

1. A method for treating or preventing pathogenic effects in a mammal caused by intracellular calcium overload, comprising administering to the mammal a mixture of sodium co-transport dependent amino carboxylic acids or their physiologically acceptable salts, in an amount sufficient to substantially saturate the sodium-dependent transport mechanisms of a cell's plasma membrane, wherein the mixture of amino carboxylic acids contain one or more substrates for a GLY transport system; one or more substrates for an A transport system; one or more substrates for an ASC transport system; one or more substrates for an N transport system; and at least one amino carboxylic acid stimulator of the mammal's hepatic urea cycle.

2. The method of claim 1, wherein the mixture amino carboxylic acids are selected from the group consisting of alanine, proline, 2-aminoisobutyric acid, N-methyl-alpha-aminoisobutyric acid, glycine, arginine, cysteine, serine, glutamine, glutamic acid, histidine, and asparagine.

3. The method of claim 2, further comprising an amino carboxylic acid capable of stimulating the mammal's hepatic urea cycle.

4. The method of claim 3, wherein the amino carboxylic acid capable of stimulating the hepatic urea cycle is arginine.

5. The method of claim 2, wherein the mixture of amino carboxylic acids is alanine, proline, histidine, serine, glycine, glutamine, glutamic acid, and arginine.

6. The method of claim 5, wherein the mixture contains from about 7 to 34 g of alanine, from about 9 to 42 g of proline, from about 8 to 28 g of histidine, from about 8 to 34 g of serine, from about 7 to 38 g of glycine, from about 5 to 34 g of glutamine, from about 1 to 9 g of glutamic acid, and from about 6 to 58 g of arginine based on a liter solution.

7. The method of claim 6, wherein the mixture contains 30 g alanine, 35 g proline, 15 g histidine, 20 g serine, 32 g glycine, 21 g glutamine, 4 g glutamic acid, and 43 g arginine.

8. The method of claim 2, wherein the step of administering further comprises an initial and a subsequent maintenance dosing of the mixture of amino carboxylic acids.

9. The method of claim 8, wherein the initial dosing ranges from about 2 to 3 ml/kg of body weight given over about 30 minutes and the maintenance dosing ranges from about 1 to 2 ml/kg/hour.

10. The method of claim 7, wherein said mixture of amino carboxylic acids is given in an initial dosage amount of 1.0 g/Kg of body weight over about 60 minutes and is given in a maintenance dosage amount of about 0.2 g/Kg/hour.

11. The method of claim 1, wherein the amino carboxylic acid mixture is administered so as to attain a blood plasma concentration of about 300 milligrams or less total free amino carboxylic acid per deciliter of blood.

12. The method of claim 1, wherein the amino carboxylic acids are administered so as to attain a blood plasma concentration of no less than about 200 milligrams total free amino carboxylic acid per deciliter of blood.

13. The method of claim 1, further comprising administering one or more therapeutically active agents selected from the group consisting of a plasma extender, a water soluble magnesium salt, thrombolytic enzyme, a scavenger of toxic oxygen metabolites, a xanthine oxidase inhibitor, and a free iron binding substance.

14. A pharmaceutical composition for treating or preventing pathogenic effects in a mammal caused by intracellular calcium overload comprising a mixture of sodium co-transport dependent amino carboxylic acids or their physiologically acceptable salts in an amount sufficient to substantially saturate the sodium-dependent transport mechanism of a cell's plasma membrane and treat or prevent said pathogenic effects, together with a pharmaceutically acceptable carrier, wherein the mixture of amino carboxylic acids contain one or more substrates for a GLY transport system; one or more substrates for an A transport system; one or more substrates for an ASC transport system; one or more substrates for an N transport system; and at least one amino carboxylic acid stimulator of the mammal's hepatic urea cycle.

15. The composition of claim 14, further comprising one or more therapeutically active agents selected from the group consisting of a plasma expander, a water soluble magnesium salt, a thrombolytic enzyme, a scavenger of toxic oxygen metabolites, a xanthine oxidase inhibitor, and a free iron binding substance.

* * * * *